United States Patent [19]
Watanabe et al.

[11] Patent Number: 6,153,413
[45] Date of Patent: Nov. 28, 2000

[54] METHOD FOR PROCESSING BACTERIAL CELLULOSE

[75] Inventors: Kunihiko Watanabe; Akira Shibata; Hiroshi Ougiya, all of Kawasaki; Nobuya Hioki, Tokyo; Yasushi Morinaga, Kawasaki, all of Japan

[73] Assignee: Bio-Polymer Research Co., Ltd., Kawasaki, Japan

[21] Appl. No.: 09/011,478

[22] PCT Filed: Jun. 9, 1997

[86] PCT No.: PCT/JP97/01949

§ 371 Date: May 27, 1998

§ 102(e) Date: May 27, 1998

[87] PCT Pub. No.: WO97/48730

PCT Pub. Date: Dec. 24, 1997

[30] Foreign Application Priority Data

Jun. 21, 1996 [JP] Japan ................................ 8-179796

[51] Int. Cl.[7] ............................ C12P 19/04; C08B 16/00
[52] U.S. Cl. .................. 435/101; 435/823; 435/277; 536/56; 536/123.12; 536/126
[58] Field of Search .................... 435/101, 823, 435/277; 536/56, 123.12, 126

[56] References Cited

U.S. PATENT DOCUMENTS

| | | | |
|---|---|---|---|
| 4,742,164 | 5/1988 | Iguchi et al. | 536/56 |
| 4,863,565 | 9/1989 | Johnson et al. | 162/150 |
| 5,207,826 | 5/1993 | Westland et al. | 106/163.1 |
| 5,228,900 | 7/1993 | Stephens et al. | 75/303 |

FOREIGN PATENT DOCUMENTS

| | | |
|---|---|---|
| 5-051885 | 3/1993 | Japan . |
| 8-127601 | 5/1996 | Japan . |
| WO 89/08148 | 9/1989 | WIPO . |

OTHER PUBLICATIONS

M. Takai, et al., Polymer Journal, vol. 7, No., 2, pp. 157–164, "Biosynthesis of Cellulose by Acetobacter Xylinum. III. .X–Ray Studies of Preferential Orientation of the Crystallites in a Bacterial Cellulose Membrane," 1975.

*Primary Examiner*—Francisco Prats
*Attorney, Agent, or Firm*—Oblon, Spivak, McClelland, Maier & Neustadt, P.C.

[57] ABSTRACT

The purpose of the present invention is to provide a convenient method for restoring the various properties of BC even after it is once dried.

The present invention relates to a method for processing a bacterial cellulose comprising dehydrating and drying under tension the bacterial cellulose produced in an agitated culture followed by homogenization, and to a method for processing a bacterial cellulose comprising dehydrating and drying the bacterial cellulose produced in an agitated culture under such conditions that a degree of planar orientation (h1/h2) (wherein h1 and h2 mean the height of a peak originating in the crystallographic plane ($1\bar{1}0$) and the crystallographic plane (110), respectively, in a diffraction curve obtained with X-ray diffractometry by a reflection method) will be 2 or more, followed by homogenization.

An excellent retention aid for fillers and sheet with a high strength may be prepared by using the bacterial cellulose obtained by the above methods.

16 Claims, 1 Drawing Sheet

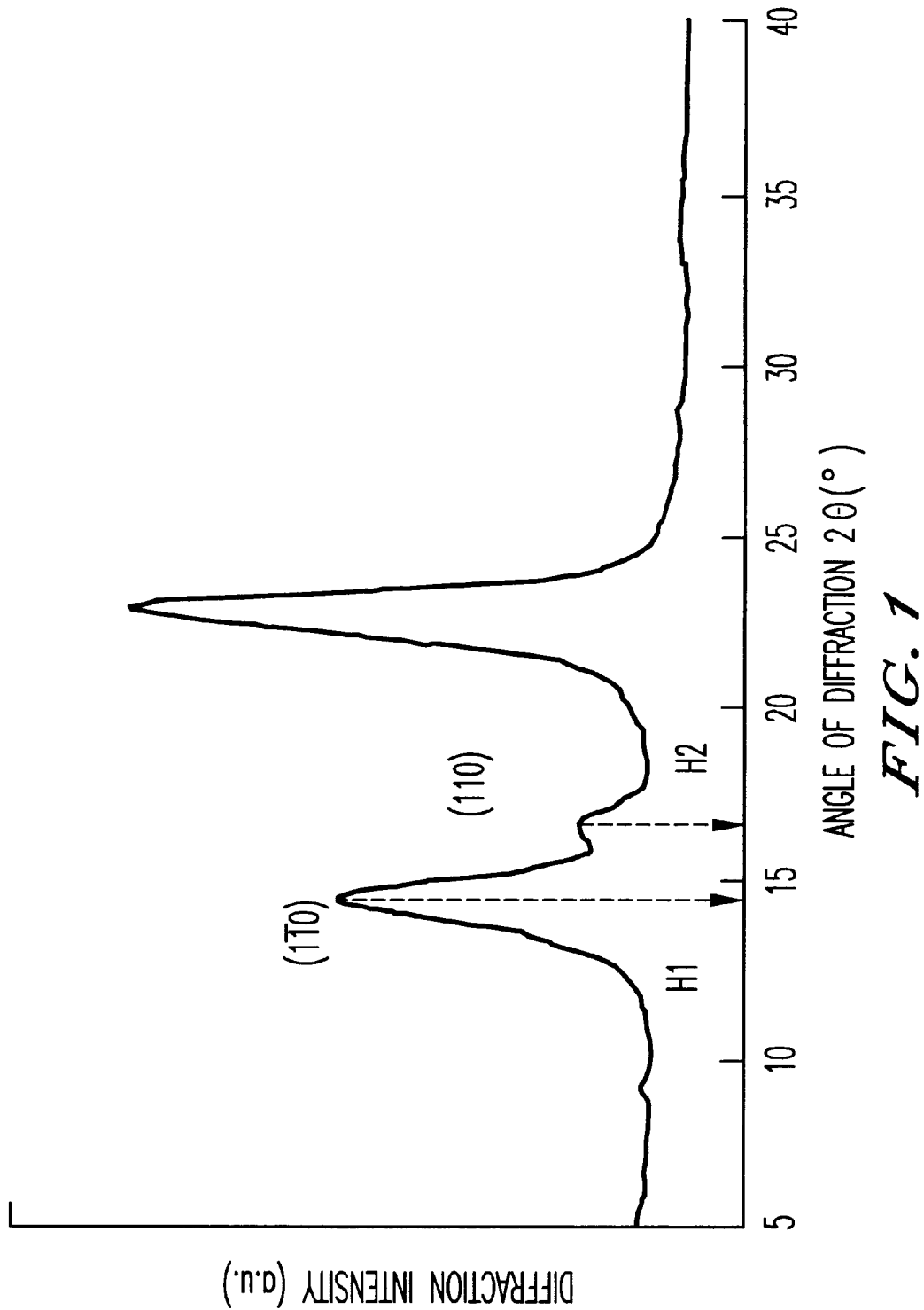

METHOD FOR PROCESSING BACTERIAL CELLULOSE

TECHNICAL FIELD

This invention relates to a method for processing a cellulosic material (bacterial cellulose: "BC") which may be produced by culturing cellulose-producing bacteria, and to a bacterial cellulose obtained by the method.

This invention also relates to a retention aid for fillers comprising homogenate of said bacterial cellulose and to a high-strength sheet comprising the same homogenate.

BACKGROUND ART

Since the bacterial cellulose is edible as well as tasteless and odorless, it is utilized in the food industry. The homogenized bacterial cellulose's high dispersibility in water further provides it with many industrial applications, such as to maintain particle sizes of food, cosmetics or coating agents, to strengthen food materials, to maintain moisture, to improve stability of food, and to be used as low-calorie additives and an emulsion stabilizer.

The bacterial cellulose is characterized by a sectional width of its fibrils which is smaller by two orders of magnitude than that of other kinds of cellulose fibers such as those derived from wood pulp.

Owing to such structural and physical feature of fibril, a homogenized bacterial cellulose has plenty of industrial applications as a reinforcing material for polymers, especially hydrophilic polymers. Products prepared by solidification of the homogenized bacterial cellulose in the form of a lump or paper show a high elastic modulus in tension owing to the above feature, and are therefore expected to have excellent mechanical properties for use in various kinds of industrial materials.

However, since an aqueous suspension or dispersion of the homogenized BC contains solvent such as water in an amount of a few to a few hundreds times the amount of cellulose component, it has some disadvantages such as the increase of space for storage, increase of the costs for storage and transportation, and decomposition of cellulose by bacteria during storage.

It is known that the characteristic features of BC will be lost upon drying. This may be attributed mainly to the following reasons:

The fibrils of BC is so fine that its surface area per volume is large. Accordingly, when moisture is evaporated from BC upon drying, a strong agglutination originating in hydrogen bonds will occur between the fibrils. Once such agglutination has occurred, the hydrogen bonds formed between the fibrils can be hardly broken off even by the addition of water. As a result, it is very hard to restore the dried BC to the original homogenate suspended in water.

In order to solve the above problems, some methods have been already proposed, whereby aqueous BC suspension is freeze-dried or solvent is substituted for water in the aqueous BC suspension followed by drying so as to avoid the formation of the hydrogen bonds between the fibrils upon drying. However, it is also well known that the above methods need a huge amount of energy and complicated processes.

In order to solve the above disadvantages, the present inventors have already proposed a method for drying a bacterial cellulose, comprising adding a third component other than water and BC to the aqueous BC suspension and dehydrating and drying (Japanese Patent Application Hei 7 (1995)-329472). According to this method, the various properties of BC such as solubility, dispersibility, precipitation degree and viscosity may be restored when BC is returned from its dry state (water content is 25% by weight or less) to its original aqueous suspension.

The present inventors have further studied other methods for solving the above disadvantages, and found that the BC's various properties may be restored by dehydrating and drying BC under tension followed by homogenization even without adding the third components.

DISCLOSURE OF INVENTION

The present invention relates to a method for processing a bacterial cellulose comprising dehydrating and drying under tension the bacterial cellulose produced in an agitated culture followed by homogenization.

The "dehydrating and drying under tension the bacterial cellulose produced in an agitated culture" means in the present specification that tension is exerted on BC during drying and dehydrating processes. It is well known that natural celluloses including BC consist of crystalline parts and amorphous parts. The former parts bind with each other through the latter ones. Upon drying, cellulose will shrink and tensile stress will be exerted on both the crystalline and amorphous parts under tension. Since elasticity is higher in the crystalline parts than in the amorphous parts, a degree of strain for the tensile stress is higher in the amorphous parts. As bonds in the amorphous parts consist of the hydrogen bonds between and within cellulose molecules, the distance between the hydrogen bonds will be enlarged due to the high degree of strain, allowing water molecules to easily penetrate into them. As a result, the hydrogen bonds between the BC fibrils with the high degree of strain will be easily broken upon the addition of water, and the hydrogen bonds between BC and water molecules, which existed before dehyrdation and drying, will be easily re-formed.

Tension during dehydration and drying may be exerted, for example, by sticking wet BC on a glass plate and the like, or casting it followed by drying. It can be also carried out by drying wet BC while keeping its shape as sheet. In the case of dying BC on the glass plate, as moisture evaporates from the upper surface of BC suspension, shrinkage accompanying drying will occur selectively only in the direction of thickness, exerting tension on BC thereby. Further, selective planar orientation will occur in the crystallographic plane (1 1̄0) in crystallographic planes of BC (the index of a crystallographic plane is expressed in accordance with monoclinic cellulose Iβ otherwise specifically noted) so that the crystallographic plane (1 1̄0) may be arranged perpendicular to the drying direction (in the direction of thickness).

Even in the case of drying BC without sticking thereof to glass, as moisture evaporates only from the upper (or back) surface of the BC sheet, shrinkage will occur selectively only in the direction of thickness of the sheet, exerting tension on BC in a similar manner as in the case of sticking BC on glass. As a result, the selective planar orientation will occur in the crystallographic plane (1 1̄0) in this case as well.

On the other hand, when BC is dried without under tension, such selective planar orientation will never occur.

Based on the above facts, the structure of the BC dried under tension may be distinguished from that of the BC dried without under tension by a degree of selective planar orientation. As mentioned above, the crystallographic plane (1 1̄0) has a tendency to be selectively planar-oriented when wet BC is dried. In other words, the BC dried under tension and formed into a shape of sheet or film has a high degree of orientation of the crystallographic plane (1$\bar{1}$0) parallel to the sheet plane. The degree of planar orientation is expressed as h1/h2 (wherein h1 and h2 mean the height of a peak originating in the crystallographic plane (1$\bar{1}$0) and the crystallographic plane (1$\bar{1}$0), respectively, in a diffraction curve obtained with X-ray diffractometry by a reflection method. The degree is at least 2, preferably 3 or more. The higher the degree of planar orientation is, the higher the selectivity of planar orientation becomes, which correlates with drying under tension.

The BC dehydrated and dried under tension according to the present invention may have various shapes such as sheet and film.

The dehydration and drying processes may be carried out by conventional methods such as drying in the air, drying with a dryer and drying under vacuum.

A drying apparatuses suitable for use in dehydration and drying of BC under tension includes continuous systems such as tunnel dryer, band dryer, tower dryer, perpendicular-turbo dryer, multidisk dryer, ventilation dryer, rotating dryer, air-flow dryer, spray dryer, drum dryer, acrew-conveyor dryer, rotating dryer with heating tube, and oscillation-transporting dryer; batch systems such as box dryer, ventilation dryer, vacuum-box dryer, and agitating dryer; and any combination thereof.

The drum dryer may be preferably used in an industrial application of the present dehydration and drying of BC. BC in a liquid state is sticked as film on the surface of the rotating drum dryer heated by medium such as steam, dried while the drum is rotating, and scraped off with a scraper-knife. As BC is dried on the drum in such a condition that the degree of planar orientation may be increased, it is considered to be dried under tension.

Thermal energy may be provided in the present drying by, for example, direct heating, indirect heating, radiant heating and the like, infrared heating and microwave heating being especially preferred in terms of energy efficiency.

By using the above apparatuses, BC may be dried into such a state that it can be restored to the original wet condition. The "dry" state in the present specification does not mean an absolutely dry state in which completely no water is contained, but means a state in which water may be contained in an amount of about 25% or less on the basis of the total weight of solid contents such as BC in the dried material. The BC in such dry state looks almost dry in appearance. The solid contents such as BC will likely adsorb moisture as they contain hydrophilic groups such as hydroxyl one in their molecules, or the solid contents with a low molecular weight have a function to maintain moisture as crystalline water. Accordingly, even the BC looking dried in appearance, which has been obtained by the above method and apparatus, will adsorb moisture in the air to reach an equilibrium state if it is allowed to stand in a usual atmosphere. If storage is needed, water activity value in the present dried BC should be controlled to such an extent that no bacterium can grow, being 0.9 at most, preferably 0.75 or less.

It is not necessary to add any specific component in dehydrating and drying BC according to the present invention. However, it is possible to add third components such as those disclosed in the Japanese Patent Application Hei 7 (1995)-329472, for example, hydrophilic liquid such as glycerin, ethylene glycol, dimethyl sulfoxide, dimethyl formamide, surfactants, lactic acid, gluconic acid and δ-gluconolactone and combination thereof; water-soluble substance such as low-molecular compounds or high-molecular compounds; and hydrophilic solid such as water-insoluble compounds and hardly water-soluble compounds.

An amount of the third component to be added may be optionally determined by those skilled in the art, depending on the kind of the material and the like, being usually in the range of from 2% by weight to 1,000% by weight of BC.

Further, the culture media of cellulose-producing bacteria per se or those further containing the third component may be used as an example of the above aqueous suspension of the bacterial cellulose. The concentration of bacterial cellulose in the aqueous suspension is significantly lower than that in the concentrate, i.e., usually between 0.01% by weight and 30% by weight, which may be optionally selected by those skilled in the art.

According to the present invention, the dehydration and drying of BC is followed by homogenization, which may be usually carried out in aqueous suspension or dispersion containing 0.01–30% by weight of BC.

The dried BC in the sheet shape, for example, may be crushed into powder with a dry crusher so that the following homogenization will be more easily carried out.

The homogenization of bacterial cellulose is considered to be a phenomenon in which the cellulose is deformed and broken under a stress induced inside the cellulose by an external force such as a mechanical force. Accordingly, the homogenization of the bacterial cellulose may be carried out by externally applying the mechanical force to the bacterial cellulose. Further, homogenization may be carried out by hydrolysis with an acid and/or alkaline substance or enzyme, or bleaching.

The mechanical force includes tensile stress, bending stress, compressive stress, torsional stress, impact stress and shearing stress. Compressive stress, impact stress and shearing stress are generally dominating.

A practical application of these mechanical forces to the bacterial cellulose may be achieved by using an appropriate apparatus such as a cooking mixer, homogenizer, blender, Polytron or ultrasonic generator.

In the homogenization using the above apparatus, the mechanical force is mainly composed of the impact force generated from the collision between agitating blades and the bacterial cellulose, and of the shearing force generated due to differences of the speed in the medium.

In the homogenization using Polytron, the mechanical force is mainly composed of the compressive force generated by sandwiching the bacterial cellulose between outer blades and inner blades, of the impact force generated from the collision between the bacterial cellulose and blades rotating at a high speed, and of the shearing stress generated in the suspension at a space between stopping outer blades and inner blades rotating at a high speed.

In the homogenization using the ultrasonic generator, the mechanical force is mainly composed of a strong shearing stress locally generated by a continuous cavitation in the suspension due to the oscillation of the ultrasonic generator.

In addition to the above embodiments, the present homogenization may be carried out in any manner for externally applying a certain load (mechanical force) to the bacterial cellulose.

Those skilled in the art may optionally select other homogenization conditions.

BC may be subjected to the above homogenization before dehydration and drying. Re-orientation during the dehydration and drying shall more easily occur by such pre-homogenization. Thus, the present "dehydration and drying under tension" may be more easily realized thereby so as to restore the various BC properties more efficiently.

The present invention also relates to a homogenized BC obtained by the present method, and to a retention aid for fillers comprising said homogenized BC, and to sheet with a high strength comprising said homogenized BC.

In the process for preparing the present sheet with excellent strength, BC is dehydrated and dried according to the present method, followed by homogenization under such a condition that restoration of the various BC properties may be partly suppressed so as not to reduce its freeness in papermaking while keeping the high strength with high Young's modulus.

The present sheet with the high strength may be prepared by any methods well known to those skilled in the art. It may contain in addition to the homogenized BC various known additives such as electrolytes, pigments, organic or inorganic compounds, sizing agents, retention aids for fillers, fluorescent agents, fungicides and anti-static agents, depending on purposes and the like.

The cellulose-producing bacteria used in the present invention may include Acetobacter strains such as *Acetobacter xylinum* subsp. sucrofermentans such as BPR 2001 strain, *Acetobacter xylinum* ATCC23768, *Acetobacter xylinum* ATCC23769, *Acetobacter pasteurianus* ATCC10245, *Acetobacter xylinum* ATCC14851, *Acetobacter xylinum* ATCC11142, *Acetobacter xylinum* ATCC10821; Agrobacterium; Rhizobium; Sarcina; Pseudomonas, Achromobacter; Alcaligenes; Aerobacter; Azotobacter; and Zooglea; and any mutants prepared by the treatment for mutagenesis with a known method using mutagens such as NTG (nitrosoguanidine).

The BPR 2001 has been deposited at the National Institute of Bioscience and Human-Technology, Agency of Industrial Science and Technology (1–3, Higashi 1-chome, Tsukuba-shi, Ibaraki-ken 350 Japan) on Feb. 24, 1993 under accession number FERM P-13466, and then transferred on Feb. 7, 1994 to the deposit under the terms of the Budapest Treaty on the International Recognition of the Deposit of Microorganisms for the Purposes of Patent Procedure and Regulation under accession number FERM BP-4545.

The chemical mutagenesis treatment using the mutagens such as NTG is described in, for example, Japanese Patent Application Hei 6(1994)-127994, Bio Factors, Vol. 1, pp.297–302 (1988) and J. Gen. Microbiol, Vol. 135, pp.2917–2929 (1989). Accordingly, those skilled in the art may obtain the present mutants in accordance with these known methods. The present mutants may be also obtained by other treatments such as application of radioactive rays.

One of the preferred examples may be a strain producing a bacterial cellulose having a weight-average degree of polymerization in terms of polystyrene of $1.6 \times 10^4$ or above, preferably $1.7 \times 10^4$ or above, which may be produced in the aerobic agitated culture; a bacterial cellulose having a weight-average degree of polymerization in terms of polystyrene of $2.0 \times 10^4$ or above, which may be produced in a static culture.

One example of the above bacteria producing bacterial cellulose with a high-degree of polymerization, BPR3001A, has been deposited at the National Institute of Bioscience and Human-Technology, Agency of Industrial Science and Technology (1–3, Higashi 1-chome, Tsukuba-shi, Ibaraki-ken 350 Japan) on Jun. 12, 1995 under accession number FERM P-14982, and then transferred on Feb. 23, 1996 to the deposit under the terms of the Budapest Treaty on the International Recognition of the Deposit of Microorganisms for the Purposes of Patent Procedure and Regulation under accession number FERM BP-5421.

It is well known that the higher the degree of polymerization is, the higher the strength and elasticity of the polymer materials become. The same is true for bacterial cellulose. The articles made from the bacterial cellulose with a high degree of polymerization will show increased strength and elasticity compared those made from the bacterial cellulose with a relatively low degree of polymerization. Thus, the bacterial cellulose with a high degree of polymerization may be advantageously used for the preparation of the articles having a high strength and elasticity.

The weight-average degree of polymerization of a various kinds of cellulose such as BC of this invention may be determined by the method using a GPC system (Tosoh HLC-8020) equipped with an RI detector as follows:

A cellulose sample is nitrated with a fuming nitric acid-phosphorous pentaoxide solution according to the method of W. J. Alexander, R. L. Mitchell, Analytical Chemistry 21, 12, 1497–1500 (1949).

Nitrated cotton linter is used as a control.

Nitrated cellulose is then dissolved in THF (Wako Pure Chemical Industries Ltd., the first grade) to a final concentration of 0.05%, and filtered through a 1.0 $\mu$m pore-size filter. THF is also used for an elution solvent.

The flow rate, pressure, and sample-injection volume are adjusted to be 0.5 ml/min., 10~13 kqf/cm$^2$ and 100 $\mu$l, respectively.

The column system consists of two TSKgel GMH-HR (S) columns (7.5 ID×300 mm) and a guard column (Tosoh Co., Ltd.). The analysis is carried out at a temperature of 35° C.

A relative molecular weight in terms of polystyrene is calculated by using polystyrene standards (Tosoh).

The polystyrene standards having a molecular weight in the range of $2.0 \times 10^7$ to 2630 are used and a standard curve is prepared based on the following three-dimension approximate equation:

$$\log M = At^3 + Bt^2 + Ct + D$$

wherein "t" is an elution time and "M" is a molecular weight.

The weight-average molecular weight and number-average molecular weight are calculated by a program (ver. 3, 10) equipped in a data processor (SC-8020).

The weight-average degree of polymerization of the original cellulose samples is finally calculated based on the above data, taking substitution degrees after the nitration into consideration.

Carbon sources in the culture media useful in the present invention include sucrose, glucose, fructose, mannitol, sorbitol, galactose, maltose, erythritol, glycerol, ethyleneglycol, ethanol and their mixtures. In addition, sucrose may be combined with starch hydrolysate containing these carbon sources, citrus molasses, beet molasses, squeezed juice from beet or sugar cane, juice from citrus and the like.

Nitrogen sources useful in the present invention include organic or inorganic ones such as ammonium salts including ammonium sulfate, ammonium chloride, ammonium phosphate; nitrates; and urea. Nitrogen-containing natural nutrients may be also used including Bacto-Peptone, Bacto-soytone, Yeast-Extract and Bean-Condensate.

A trace amount of organic nutrients may be further added including amino acids, vitamins, fatty acids, nucleic acids, 2,7,9-tricarboxy-1H pyrrolo [2,3,5]-quinoline-4,5-dione, sulfite pulp waste liquor, lignin sulfonic acid and the like.

When the mutants with the nutritional requirement for amino acids are used, such required nutrients should be supplemented in the culture media. Inorganic nutrients include phosphate salts, magnesium salts, calcium salts, iron salts, manganese salts, cobalt salts, molybdate salts, hematite salts, chelate metal salts and the like.

It is also possible to optionally supply accelerators for the cellulose production such as inositol, phytic acid, pyrroloquinoline quinone (PQQ) (Japanese Patent Publication Hei 5(1993)-1718; Mitsuo TAKAI, Japan TAPPI Journal, Vol.42, No.3, pp.237–244), carboxylic acid or their salts (Japanese Patent Laid-Open Application Hei 7(1995)-39386, laid open Feb. 10, 1995), invertase (Japanese Patent Laid-Open Application Hei 7(1995)-184677, laid open Jul. 25, 1995) and methionine (Japanese Patent Laid-Open Application Hei 7(1995)-184675, laid open Sep. 25, 1995) into the culture media.

For example, when the Acetobacter is used as the cellulose-producing bacteria, a pH range for the culture is controlled between 3 and 7, preferably around 5. A culture temperature is kept in a range between 10 and 40° C., preferably between 25 and 35° C. Oxygen supply into a culturing apparatus may contain from 1 to 100% oxygen, desirably 21 to 80%. Those skilled in the art may optionally determine the contents of these components in the culture media and amounts of the bacteria to be inoculated into the media, depending on the culture method to be used.

Further, the present inventors have found that BC produced in an agitation culture is suitable for the present invention. It is known that BC produced in the agitation culture (Agitated BC) has a relatively disordered structure in various aspects such as degrees of crytallization and polymerization when compared to BC produced in a usual static culture (Static BC). Such disordered structure is considered to originate in the amorphous parts. Since the degree of strain for the tensile stress is higher in the amorphous parts as already mentioned, the BC produced in the agitation culture will be more significantly effected by the present dehydration and drying under tension and more easily restore its various properties.

The present BC may be produced in any known aerobic agitated culture conditions, as described above. Any known culture operation method such as batch fermentation, fed batch fermentation, repeated batch fermentation and continuous fermentation may be adopted.

The agitated culture is carried out under agitation of the culture medium. Said agitation operation during the agitated culture may change the structure of the bacterial cellulose into, for example, an more amorphous one having a lower crystallinity.

Means for agitation include impellers, air-lift fermenters, pump-driven recirculation of the fermenter broth and any combination of these means.

Further, the bacterial cellulose may be also produced by the method described in Japanese Patent Laid-Open Application Hei 8(1996)-33494 (laid open Feb. 6, 1996) in the name of the present applicant, wherein culture media containing bacteria are circulated between a culturing apparatus and a separator to separate the resulting bacterial cellulose from the bacteria and culture media in said separator, or by the method described in Japanese Patent Laid Open Application Hei 8(1996)-33495 (laid open Feb. 6, 1996) in the name of the present applicant, wherein the concentration of the bacterial cellulose in culture media is kept at a lower level by a continuous removal of the culture media from its culture system and a continuous supply of fresh culture media having almost the same volume as the removed culture media.

The agitated culture may be carried out in any culturing apparatus with agitation, such as a jar fermenter, tank, baffle flask, slanted-baffle flask and air-lift fermenter.

In the present agitated culture, gas may be optionally passed through the culture media. Such gas includes oxygen-containing gas such as air, as well as gas free of oxygen such as argon or nitrogen. Those skilled in the art may optionally select the gas to be passed, depending on the culture conditions.

For example, when anaerobic bacteria are used, an inert gas may be passed through the culture media so that the bubbles thereof will agitate the culture media.

When aerobic bacteria are used, an oxygen-containing gas may be passed through the culture media to supply oxygen required for the growth of the bacteria. The bubbles thereof will also agitate the culture media.

The bacterial cellulose obtained in the agitated culture may be separated from the culture media by using the centrifugation or filtration method.

The bacterial cellulose may be recovered together with the bacteria, and then impurities other than the bacterial cellulose, including the bacteria per se, may be removed from the recovered bacterial cellulose.

The impurities may be almost completely removed from the bacterial cellulose by washing, dehydration under pressure, dilute acid washing, alkali washing, bleaching with hypochlorite soda or hydrogen peroxide, lysing with lytic enzymes such as lysozyme, treatment with surfactants such as sodium lauryl sulfate or sodium deoxycholate, washing under heat at a temperature range between a room temperature and 200° C., and any combination of these treatments.

The bacterial cellulose thus obtained according to the present invention includes cellulose, those comprising heteropolysaccharides having cellulosic main chains, and those comprising β-1,3- or β-1,2-glucan. Said heteropolysaccharides contain as components hexoses, pentoses and organic acids such as mannose, fructose, galactose, xylose, arabinose, rhamnose and glucuronic acid, as well as glucose.

These polysaccharides may be present alone or as a mixture combined each other via hydrogen bonds.

BRIEF DESCRIPTION OF DRAWING

FIG. 1 shows an example of X-ray diffraction curve obtained with X-ray diffractometry on a dry BC sample by the reflection method.

BEST MODE FOR CARRYING OUT THE INVENTION

The present invention will be further illustrated by the following examples, which should not be construed to limit the scope of the present invention. In the following examples, the BC content (%) means the "% by weight" unless particularly otherwise remarked.

The properties are determined as follows.
Dispersibility:
Dispersibility of the suspension of the homogenized BC is observed and compared with the naked eye before and after drying.
Precipitation Degree After Centrifugation:
Precipitation degree is represented in terms of a volume ratio of a precipitated bacterial cellulose to the total volume, after the aqueous suspension (10 ml) containing 0.2% of BC in a tube (15 ml, Falcon) is centrifuged at 3,000 rpm for 15 minutes. The greater the value of precipitation degree shows, the higher dispersibility is, meaning that the suspended BC will hardly precipitate and be dispersed well.

Viscosity:

The "viscosity" in the present specification means an absolute value of complex viscosity that is obtained with respect to the aqueous suspension of BC (0.1%) in a dynamic liquid viscoelasticity measuring apparatus "FLUIDS SPECTROMETER RFS II" (Rheometric Scientific Ltd.) at an angular frequency of 10 rad/sec and 30° C., and shown as follows:

Absolute value of complex viscosity (P) $|\eta^*|=|G^*|/\omega|G^*|=(G'^2+G''^2)^{1/2}$ wherein $|G^*|$: absolute value of complex modulus (dyn/cm$^2$)

$G'$: storage modulus (dyn/cm$^2$)

$G''$: loss modulus (dyn/cm$^2$)

$\omega$: angular frequency in the oscillation of paralell discs (rad/s).

Specifically, 2 ml of an aqueous suspension containing 0.1% of the homogenized BC is sandwiched between parallel discs having a diameter of 5 cm. Under the conditions of a temperature of 30° C. and strain of 10% in Frequency Sweep mode, the discs are oscillated at ten increasing steps of an angular frequency in the range of from 1 to 100 rad/s, and viscosity was then measured at an angular frequency of 10 rad/s. The strain is represented by the following equation:

Strain (%)$\gamma$=R/H×$\theta$×100 wherein

R : radius of the parallel discs (mm)

H : thickness of the sample between the discs (mm)

$\theta$: angular displacement of the parallel discs (rad)

Production and Homogenization of Bacterial Cellulose (Reference Example)

(1) Preparation of a Seed Bacteria Solution (growth of bacteria)

The cellulose-producing bacteria were grown in a flask culture.

A Roux flask (750 ml volume) containing 100 ml of a base medium consisting of fructose (40 g/L), potassium phosphate (1.0 g/L), magnesium sulfate (0.3 g/L), ammonium sulfate (3 g/L), Bacto-Peptone (5 g/L) and lactic acid (1.4 ml/L) was inoculated with 1 ml of a cryopreserved bacteria solution of BPR 2001 (FERM BP-4545) at an initial pH of 5.0. The bacteria were incubated in an incubator at 28° C. for three days under a static culture condition. After the completion of the seed culture, the Roux flask was vigorously shaken and aseptically filtered through a gauze to obtain the seed bacteria solution.

(2) Production of Bacterial Cellulose in the Agitated Culture 60 ml of the above seed bacteria solution was aseptically inoculated into 540 ml of a sterilized culture medium for the agitated culture in a small jar fermenter (1000 ml total volume). The bacteria were cultured at 30° C. for 20 or 30 hours and at an initial agitation rate of 400 rpm, while adjusting a pH to 5.0 by the addition of ammonia gas or 1N $H_2SO_4$ and maintaining an amount of dissolved oxygen (DO) between 3.0 and 21.0% by automatically controlling the agitation rate.

The following CSL-Fru medium was used for the agitated culture.

TABLE 1

| CSL-Fru medium | | |
| --- | --- | --- |
| Fructose | 4.0 | (%) |
| $KH_2PO_4$ | 0.1 | |
| $MgSO_4.7H_2O$ | 0.25 | |
| $(NH_4)_2SO_4$ | 0.33 | |
| Vitamin Mixture (see below) | 1.0 | |
| Salt Mixture (see below) | 1.0 | |
| CSL (Corn Steep Liquor) | 2.0 | |
| an initial pH of 5.0 | | |

TABLE 2

| Salt Mixture | |
| --- | --- |
| $FeSO_4.7H_2O$ | 360 mg/l |
| $CaCl_2.2H_2O$ | 1470 mg/l |
| $Na_2MoO_2.2H_2O$ | 242 mg/l |
| $ZnSO_4.7H_2O$ | 173 mg/l |
| $MnSO_4.5H_2O$ | 139 mg/l |
| $CuSO_4.5H_2O$ | 5 mg/l |

TABLE 3

| Vitamin Mixture | |
| --- | --- |
| compound | mg/L |
| Inositol | 200 |
| Niacin | 40 |
| Pyridoxine HCl | 40 |
| Thiamine HCl | 40 |
| Ca Pantothenate | 20 |
| Riboflavin | 20 |
| p-Aminobenzonic Acid | 20 |
| Folic Acid | 0.2 |
| Biotin | 0.2 |

After the completion of the culture, solid mass accumulated in the jar fermenter were collected and washed with water to remove the medium components. The solid mass were then washed with 1% NaOH aqueous solution at 80° C. for overnight to remove the bacteria. The solid mass were then neutralized with sulfuric acid and washed with water until its pH reached a neutral range to give a purified bacterial cellulose.

(3) Production of Bacterial Cellulose in the Static Culture

The same culture medium (600 ml) as in the above (2) was divided into 30 ml each in a sterilized petri dish and used in the static culture at 30° C. for seven days. After the completion of the culture, BC produced at the surface of the petri dish was washed with water to remove the culture components.

The above concentration of BC was measured as follows:

Solid contents in a wet state were separated from the culture broth by centrifugation, soaked at 100° C. for one hour in a 0.2 N NaOH solution of an amount of 20 times the separated solids contents to remove the bacterial cells and other culture ingredients from the bacterial cellulose, washed throughly, and dried. The thus dried BC was then weighed.

EXAMPLE 1

The agitated BC or static BC (5 parts) prepared in Reference Example was mixed with water (95 parts) and the resulting mixture (250 ml) was homogenized at 18,000 rpm for 2 min. by means of a blender (Oster blender manufactured by SUNBEAM-OSTER HOUSEHOLD PRODUCTS Co.) to give the suspension containing 0.5% homogenized BC. Precipitation degree of the suspension was determined. The suspension of the homogenized BC was then taken into a polypropylene tube (ca. 4 cm in diameter) to the depth of about 5 mm, dried at 105° C. by means of infrared to give sheet. The thickness of the resuting sheet was about 30 μm or less. The sheet (20 mg) was mixed with water (10 ml) and homogenized by means of Physcotron (Niti-on Medical & Physical Instruments Mfg. Co.) at a maximum speed for one min. Precipitation degree of the resulting homogenate was also determined. Such drying into sheet followed by homogenization was repeated for several times and Precipitation degree was determined after each repeating cycle. The results are shown in TABLE 4.

TABLE 4

| The number of times | Precipitation degree (%) | |
|---|---|---|
| | Static BC | Agitated BC |
| 0 (no drying) | 18 | 40 |
| 1 | 8 | 41 |
| 2 | 8 | 40 |
| 3 | 7 | 50 |
| 4 | 7 | 56 |
| 5 | 9 | 61 |

It is found that the agitated BC dried in the sheet shape is superior to the dried static BC in restoration of the properties. Furthermore, the repetition of drying and homogenization cycles will increase precipitation degree of the agitated BC over that of the original homogenized BC. The suspension of the agitated BC is excellent also in dispersibility observed with the naked eye.

EXAMPLE 2

Dry sheet was prepared from the agitated BC of Reference Example that had been homogenized in accordance with in EXAMPLE 1, and from the same agitated BC that had been only suspended into water without homogenization. The resulting dry sheet was then homogenized and their precipitation degree was determined. The results are shown in TABLE 5.

TABLE 5

| | Precipitation degree (%) | |
|---|---|---|
| | Homogenized BC | Non-homogenized BC |
| No drying | 33 | 8 |
| Drying and homogenization | 45 | 14 |

It is found that the restoration owing to the drying and homogenization is more increased by homogenization before drying into sheet. The dispersibility showed a similar tendency.

EXAMPLE 3

The agitated BC prepared as Example 1 was casted onto an aluminum plate, and absolutely dried by infrared at 105° C. The same BC sample containing 0.2% by weight of the homogenized BC was spray-dried by means of SPRAY Dryer DL-41 manufactured by YAMATO SCIENCE Co. under the conditions of Inlet temp. of 270° C., Outlet temp. of 90° C., flow rate of the suspension of the homogenized BC of 20 g/min., and air flow rate of 0.6~0.7 m³/min. The same BC sample was also frozen rapidly with liquid nitrogen and dried. These three kinds of dry samples were subjected to homogenization according to the method of Example 1.

These three dry samples were examined in X-ray diffractometry to obtain the degree of planar orientation. The freeze-dried and spray-dried BC samples were pressed under 200 kg/cm² to form a tablet which was then subjected to the X-ray diffractometry, while the BC sheet samples were examined as such. The X-ray diffractometry was carried out by the reflection method with Geiger Flex 2027 (Rigaku Co.) at 35 kv, 20 mA and 2θ being in the range of from 50° to 40°. The degree is expressed as h1/h2, wherein h1 and h2 mean the height of a peak originating in the crystallographic plane ($1\bar{1}0$) and the crystallographic plane ($1\bar{1}0$), respectively, in the diffraction curve obtained with X-ray diffractometry by a reflection method. The thickness of the sheet samples represents an average value calculated on five values determined with a micrometer. The results are shown in TABLE 6.

TABLE 6

| Shape of the dry sample | Degree of Precipitation (%) | Degree of planar Orientation (−) |
|---|---|---|
| Sheet (40 μm thickness) | 26 | 4.1 |
| Sheet (350 μm thickness) | 20 | 3.9 |
| Spray-dried powder | 2 | 1.5 |
| Freeze-dried sample | 38 | 1.4 |

Since the fine cellulose fibrils do not bind together in the freeze-dried sample, the degree of precipitation of the aqueous suspension obtained by the homogenization of the above sample was almost the same level as that of the original suspension of the homogenized BC (without drying). On the other hand, the fibrils are bound with each other in the spray-dried sample, water can not pass into the fibrils even after the homogenization of the dry sample, and the degree of precipitation is not therefore restored. The similar tendency is observed in dispersibility. In the case of dry sheet samples wherein the bondings between fibrils are strong, it is considered that since BC has been dried under tension as seen from the high degree of planar orientation, penetrating water molecules will easily break hydrogen bonds so as to recover the degree of precipitation in the homogenized dry sheet samples.

EXAMPLE 4

The agitated BC homogenate prepared as Example 1 was diluted with water to a final concentration of 0.2% and subjected to viscosity determination to give 8.8729 poise. The same sample was dried into sheet and homogenized again according to Example 1, followed by determination of viscosity to give 8.7124 poise. These results show that drying of the homogenized BC into sheet followed by homogenization will restore viscosity.

EXAMPLE 5

The agitated BC homogenized as Example 1 was dried with a drum dryer (KDS1 manufactured by Kusuki Kikai Seisakusho Co.) into sheet. The dried sheet sample was homogenized according to Example 2 to determine its degree of precipitation. The result showed that the degree of precipitation of the dried sample was higher than that of the original homogenized BC, as seen in TABLE 5.

EXAMPLE 6

Evaluation of filler retention

The agitated BC homogenized as Example 1 was dried with the drum dryer (KDS1 manufactured by Kusuki Kikai Seisakusho Co.) into flakes, which were then crushed with a dry crusher to give dry powder and homogenized according to the method of Example 2. 100 parts of light calcium carbonate and 1 part of cationic starch were added to 100 parts of a pulp which had been obtained by mixing the resulting homogenate with bleached hardwood kraft pulp homogenized in accordance with JIS-P-8209 at a weight ratio of 5:95. Filler retainablity was determined from an amount of those that had passed through a filter in accordance with TAPPI standard method T261. The weight of the fillers was measured by ashing them at 400° C. for 8 hours in accordance with TAPPI standard method T269. The results are shown in TABLE 7

TABLE 7

|  | BC contents (%) | Filler Retainability (%) |
| --- | --- | --- |
| Blank (no BC) | 0 | 16.8 |
| BC dry flakes | 5 | 32.2 |
| BC dry powder | 5 | 16.4 |
| Control (no drying) | 5 | 30.6 |

The above results show that the addition of the BC homogenate obtained according to the present invention will significantly increase filler retainability in a similar manner to the non-dried BC homogenate.

EXAMPLE 7

The agitated BC obtained in Reference Example was mixed with water and homogenized at 18,000 rpm for 2 min. by means of a blender (Oster blender manufactured by SUNBEAM-OSTER HOUSEHOLD PRODUCTS Co.) to give suspension containing 0.5% homogenized BC. The suspension of the homogenized BC was then taken into a polypropylene dish (ca. 4 cm in diameter) to the depth of about 5 mm, dried at 105° C. by means of infrared to give a sheet sample. The thickness of the resulting sheet was about 30 $\mu$m or less. The suspension of the homogenized BC was also freeze-dried under vacuum to give a lump of the sample BC.

The sheet sample (20 mg) was mixed with water (10 ml) and homogenized by means of Physcotron (Niti-on Medical & Physical Instruments Mfg. Co.) at a maximum speed for two min. The same procedure was repeated to finally obtain a large amount of the suspension of the homogenate (1). A large amount of the suspension of the homogenate (2) was similarly prepared by using the lump of the sample BC.

The original homogenized BC without being dried (control), the above homogenate (1) and homogenate (2) were then taken into a polystyrene dish (ca. 4 cm in diameter) to the depth of about 5 mm, dried at 50° C. by means of infrared to give a sheet sample. Each resulting sheet was peeled off and determined with respect to their thickness. A strip of 5 mm in width and 3 cm in length was excised from each sheet and subjected to the determination of Young's modulus in a longitudinally oscillation method at a room temperature, frequency by of 10 Hz, initial tension of 100 g, displacement of 10 $\mu$m and sample length of 2 cm by using DMS210 (SEIKO ELECTRONICS Co.).

Freeness of the above three samples was also determined. 50 ml of the suspension containing 0.2% of each homogenated BC was aspirated through a filter paper of 47 mm in diameter (Advantec Toyo Co., No.2), and an amount of water filtered for the first 10 min. was determined.

The results are shown in TABLE 8. An apparent specific gravity was calculated from the weight, thickness, width and length of the samples.

TABLE 8

|  | Control | Homogenate (1) | Homogenate (2) |
| --- | --- | --- | --- |
| Thickness ($\mu$m) | 50.6 | 42.4 | 54.2 |
| Apparent specific gravity | 0.83 | 0.73 | 0.70 |
| Young's modulus (GPa) | 18.6 | 14.5 | 13.1 |
| Corrected Young's modulus (GPa)* | 36.0 | 31.6 | 29.7 |
| Freeness (ml/min.) | 11.25 | 18.50 | 27.50 |

Corrected Young's modulus (GPa)* is a value which is obtained by dividing the determined Young's modulus by the apparent specific gravity and multiplying the quotient by the specific gravity of cellulose (1.59).

Corrected Young's modulus (GPa)* is a value which is obtained by dividing the determined Young's modulus by the apparent specific gravity and multiplying the quotient by the specific gravity of cellulose (1.59).

Industrial Applicability

By using the BC dried and homogenized according to the present invention, an excellent retention aid for fillers may be prepared. Further, the sheet prepared from said BC has a greatly increased freeness, while its Young's modulus is substantially the same as that of the sheet prepared from the homogenized BC without drying. These results show that the present BC dried and homogenized according to the present invention may be advantageously used especially in terms of freeness in the process of sheet with a high strength.

What is claimed is:

1. A method for processing a bacterial cellulose comprising, in order, (1) subjecting bacterial cellulose produced in an agitated culture to homogenization, (2) dehydrating and drying under tension said bacterial cellulose, and (3) homogenizing.

2. A method for processing a bacterial cellulose comprising, in order, (1) subjecting bacterial cellulose produced in an agitated culture to homogenization, (2) dehydrating and drying said bacterial cellulose produced in an agitated culture under such conditions that a degree of planar orientation (h1/h2) (wherein h1 and h2 mean the height of a peak originating in the crystallographic plane ($1\bar{1}0$) and the crystallographic plane ($1\bar{1}0$), respectively, in a diffraction curve obtained with X-ray diffractometry by a reflection method) will be 2 or more, and (3) homogenizing.

3. A method according to claim 1, wherein homogenizing is carried out by mechanical shearing force, ultrasonic, high pressure, hydrolysis with an acid substance or enzyme, bleaching, or any combination thereof.

4. A method according to claim 1, wherein dehydration and drying are carried out by a drum dryer, pressing, drying in the air, drying with a dryer, drying under vacuum or any combination thereof.

5. A method according to claim 1 wherein the bacterial cellulose produced in an aerobic agitated culture and having a weight-average degree of polymerization in terms of polystyrene of $1.6 \times 10^4$ or above is used.

6. A method for processing a bacterial cellulose comprising, in order, (1) subjecting bacterial cellulose produced in a static culture and having a weight-average degree of polymerization in terms of polystyrene of $2.0 \times 10^4$ or above to homogenization, (2) dehydrating and drying under tension said bacterial cellulose, and (3) homogenizing.

7. An aqueous suspension of the bacterial cellulose prepared according to any one of the method of claim 1.

8. A retention aid for fillers comprising the bacterial cellulose of claim 7.

9. Sheet having a Freeness of 18.50 (ml/min.) or more prepared from the bacterial cellulose of claim 7.

10. A method according to claim 2, wherein homogenizing is carried out by mechanical shearing force, ultrasonic, high pressure, hydrolysis with an acid substance or enzyme, bleaching, or any combination thereof.

11. A method according to claim 2, wherein dehydration and drying are carried out by a drum dryer, pressing, drying in the air, drying with a dryer, drying under a vacuum or any combination thereof.

12. A method according to claim 2, wherein the bacterial cellulose produced in an aerobic agitated culture and having a weight-average degree of polymerization in terms of polystyrene of $1.6 \times 10^4$ or above is used.

13. A method for processing a bacterial cellulose comprising, in order, (1) subjecting bacterial cellulose produced in a static culture and having a weight-average degree of polymerization in terms of polystyrene of $1.6 \times 10^4$ or above to homogenization, (2) dehydrating and drying under tension said bacterial cellulose, and (3) homogenizing.

14. An aqueous suspension of the bacterial cellulose prepared according to claim 2.

15. A retention aid for fillers comprising the bacterial cellulose of claim 14.

16. Sheet having a Freeness of 18.50 (ml/min.) or more prepared from the bacterial cellulose of claim 14.

* * * * *